United States Patent
Li et al.

(10) Patent No.: US 10,479,759 B2
(45) Date of Patent: Nov. 19, 2019

(54) SYNTHETIC METHODS FOR THE PREPARATION OF PROPYLENE AMMOXIDATION CATALYSTS

(71) Applicant: Clariant Corporation, Louisville, KY (US)

(72) Inventors: Hailian Li, Union City, CA (US); Claus G. Lugmair, Santa Cruz, CA (US)

(73) Assignee: Clariant Corporation, Louisville, KY (US)

( * ) Notice: Subject to any disclaimer, the term of this patent is extended or adjusted under 35 U.S.C. 154(b) by 178 days.

(21) Appl. No.: 15/427,331

(22) Filed: Feb. 8, 2017

(65) Prior Publication Data
US 2018/0222850 A1    Aug. 9, 2018

(51) Int. Cl.
| | |
|---|---|
| C07C 253/26 | (2006.01) |
| B01J 23/00 | (2006.01) |
| B01J 23/889 | (2006.01) |
| C07C 45/35 | (2006.01) |

(52) U.S. Cl.
CPC ........... *C07C 253/26* (2013.01); *B01J 23/002* (2013.01); *B01J 23/8898* (2013.01); *C07C 45/35* (2013.01); *B01J 2523/00* (2013.01)

(58) Field of Classification Search
CPC ..... B01J 23/002; B01J 23/8898; C07C 45/35; C07C 253/26
See application file for complete search history.

(56) References Cited

U.S. PATENT DOCUMENTS

| | | |
|---|---|---|
| 3,471,545 A | 10/1969 | Giordano |
| 3,691,096 A | 9/1972 | Sennewald |
| 3,833,649 A | 9/1974 | Wada |
| 4,040,978 A | 8/1977 | Li |
| 4,168,246 A | 9/1979 | Li |
| 4,377,534 A | 3/1983 | Grasselli |
| 4,638,029 A | 1/1987 | Meschke |
| 4,728,705 A | 3/1988 | Nestlerode |
| 4,766,232 A | 8/1988 | Grasselli |
| 4,863,891 A | 9/1989 | Grasselli |
| 5,093,299 A | 3/1992 | Suresh |
| 5,198,578 A | 3/1993 | Etzkorn |
| 5,212,137 A | 5/1993 | Suresh |
| 5,223,469 A | 6/1993 | Chen |
| 5,290,745 A | 3/1994 | Jorgensen |
| 5,306,350 A | 4/1994 | Hoy |
| 5,604,172 A | 2/1997 | Wagner |
| 5,658,842 A | 8/1997 | Midorikawa |
| 5,663,112 A | 9/1997 | Ahn |
| 5,663,113 A | 9/1997 | Midorikawa |
| 5,716,558 A | 2/1998 | Nielsen |
| 5,870,664 A | 2/1999 | Sata |
| 6,136,998 A | 10/2000 | Sasaki |
| 6,437,193 B1 | 8/2002 | Contractor |
| 6,462,232 B1 | 10/2002 | Nakamura |
| 6,946,422 B2 | 9/2005 | Stevenson |
| 6,982,236 B2 | 1/2006 | Wenzel |
| 7,341,974 B2 | 3/2008 | Kang |
| 7,365,041 B2 * | 4/2008 | Miyaki ............ B01J 21/08 502/206 |
| 7,473,666 B2 | 1/2009 | Yanagi |
| 7,544,633 B2 | 6/2009 | Kang |
| 7,576,232 B2 | 8/2009 | Seely |
| 7,615,509 B2 | 11/2009 | Bai |
| 8,480,998 B2 | 7/2013 | Hagemeyer |
| 2016/0051967 A1 | 2/2016 | Sokolovskii |

FOREIGN PATENT DOCUMENTS

| | | | | |
|---|---|---|---|---|
| CN | 1393285 A | * | 1/2003 | ............ B01J 23/889 |
| WO | WO-2014169163 A1 | * | 10/2014 | ............ B01J 23/8885 |

OTHER PUBLICATIONS

Jin, Sheng-Ming Journal of Central South University of Technology (English Edition) (2004), 11(4), 395-399.
Wang, Yang, Chinese Chemical Letters (2011), 22(11), 1321-1325.
U Young Jo, Applied Catalysis A:General (2009), 358, 180-185.
Duc Truong, Res Chem Intermed (2011), 37, 605-616.
Y. Yoshimura, Applied Catalysis A: General (1991), 79, 145-159.
Ji Chul Jung, Catal. Lett. (2009), 128, 243-247.

* cited by examiner

*Primary Examiner* — Joseph R Kosack

(57) ABSTRACT

The present disclosure relates generally to catalyst materials and processes for making and using them. More particularly, the present disclosure relates to molybdenum, bismuth and iron-containing metal oxide catalyst materials useful, for example, in the partial oxidation or ammoxidation of propylene or isobutylene, processes for making them, and processes for making acrolein, methacrolein, acrylonitrile, and methacrylonitrile using such catalysts.

21 Claims, 2 Drawing Sheets

SYNTHETIC METHODS FOR THE PREPARATION OF PROPYLENE AMMOXIDATION CATALYSTS

BACKGROUND OF THE DISCLOSURE

1. Field of the Disclosure

The present disclosure relates generally to catalyst materials and processes for making and using them. More particularly, the present disclosure relates to molybdenum, bismuth and iron-containing metal oxide catalyst materials useful, for example, in the partial oxidation or ammoxidation of propylene or isobutylene, processes for making them, and processes for making acrolein, methacrolein, acrylonitrile, and methacrylonitrile using such catalysts.

2. Technical Background

Molybdenum-iron-bismuth oxide catalysts have conventionally been used for the reaction of propylene or isobutylene with ammonia and oxygen to make acrylonitrile or methacrylonitrile. Such "ammoxidation" reactions are typically performed at high temperature in the gas phase, often in fluidized bed reactors. The catalyst materials themselves often include a variety of additional elements, such as cerium, cobalt, potassium, cesium, chromium, antimony, as promoters to increase the catalytic efficacy of the catalytic material. The catalyst materials are conventionally made in a batch process by coprecipitation of metal containing precursors such as nitrates with ammonium molybdate and a silica sol, followed by spray-drying of the resulting slurry and calcining of the resulting particles to provide oxide material. More complex multiple-step preparations are also known. Conventional catalysts are produced, for example, by a Pechini process or a sol-gel process.

A key feature of conventional production processes is the formation of loose particles of catalytically-active metal oxide material, which must be brought into a certain form or applied to a substrate in order to be suitable for catalytic use (e.g., in fixed bed or fluid bed processes). In addition, the conventional production processes provide loose particulate catalytically active material having a large pore volume, which can be detrimental to the mechanical strength of the material. For this reason, in the conventional production processes, additives such as glass fibers are typically added to the loose catalytically active material before it is shaped in order to enhance the mechanical properties of the final catalyst.

The conventional production processes for catalysts for the partial oxidation of olefins also share the common feature that they include precipitation or gelling of the catalytically active components to form a slurry or a gel. As a result, a uniform catalyst material is difficult to achieve because the catalytically active components situated within the solid particles are not able to react with other components that are present in the solution. In addition, the catalytically active components situated within the solid particles are not available for the oxidation reaction to be catalyzed, so that only a small portion of the catalytically active components is in contact with the reaction mixture and thus actually catalyzes the oxidation reaction, which of course not only impairs the efficiency of the catalytically active components that are used, but also decreases the conversion rate of the oxidation reaction to be catalyzed and, thus, reduces the yield of the desired product.

SUMMARY OF THE DISCLOSURE

There remains a need for improved partial oxidation and/or ammoxidation catalysts that provide not only acceptable efficiency of the catalyst, but also desirable activity (e.g., overall reaction of propylene or isobutylene starting material) and desirable selectivity (e.g., fraction of reacted starting material converted to acrylonitrile or methacrylonitrile). The inventors have found simple and cost-efficient processes for preparing highly efficient catalysts suitable for partial oxidation and/or ammoxidation of olefins, such as propylene or isobutylene.

Thus, one aspect of the disclosure provides a process for producing a catalyst material, the catalyst material comprising a metal oxide catalyst in an amount in the range in an amount of at least about 25 wt %, the metal oxide catalyst having the formula $Mo_xBi_yFe_zA_aB_bC_cD_dO_v$, wherein x is in the range of 10 to 14;

y is in the range of 0.05 to 5;

z is in the range of 0.2 to 5;

A is at least one element selected from Ni and Co;

a is in the range of 1 to 10;

B is at least one element selected from the lanthanides, Mg, Cr, Mn, Zn and Ca;

b is in the range of 0.01 to 6;

C is at least one element selected from W, Sn, V, Ti, Zr, Ga, Hf, Nb, Ta, In and Al;

c is in the range of 0 to 8;

D is at least one element selected from Li, Na, K, Rb and Cs;

d is in the range of 0.02 to 2; and v is the number of oxygen atoms required to satisfy the valence requirements of the other component elements Mo, Bi, Fe, A, B, C, and D, the process comprising:

providing a suspension or slurry of an inert carrier in a metal oxide precursor fluid comprising a solvent in admixture with a plurality of metal oxide precursors, the plurality of metal oxide precursors comprising at least a molybdenum oxide precursor, a bismuth oxide precursor, and an iron oxide precursor, spray drying the suspension or slurry of the inert carrier in the metal oxide precursor fluid to obtain a spray-dried precursor material; and heating the spray-dried precursor material to obtain the catalyst material.

In certain such embodiments, the catalyst can further include an inert carrier having a specific surface of 1 to 500 m²/g in an amount up to 75 wt % of the catalyst material, e.g., in an amount in the range of about 25 wt % to about 75 wt % of the catalyst material. In such embodiments, a suspension or slurry of the inert carrier in the metal oxide precursor fluid can be provided (e.g., by combining the inert carrier with the metal oxide precursor fluid), which is spray dried as described above.

The processes described herein can be used with a variety of mixed metal oxide catalysts. For example, the metal oxide catalyst can be a molybdenum-containing mixed metal oxide. In certain embodiments, the mixed metal oxide is of the formula $Mo_xBi_yFe_zA_aB_bC_cD_dO_v$, wherein
x is in the range of 10 to 14;
y is in the range of 0.05 to 5;
z is in the range of 0.2 to 5;
A is at least one element selected from Ni and Co;
a is in the range of 1 to 10;
B is at least one element selected from the lanthanides, Mg, Cr, Mn, Zn and Ca;
b is in the range of 0.01 to 6;
C is at least one element selected from Sn, V, Ti, Zr, Ga, Hf, Nb, Ta, In and Al;
c is in the range of 0 to 8;
D is at least one element selected from Li, Na, K, Rb and Cs;
d is in the range of 0.02 to 2; and
v is the number of oxygen atoms required to satisfy the valence requirements of the other component elements Mo, Bi, Fe, A, B, C, and D.

In another aspect, the disclosure provides a process for the conversion of propylene, isobutylene, or a mixture thereof to acrylonitrile, methacrylonitrile, or a mixture thereof, the process including reacting the propylene, isobutylene, or the mixture thereof with ammonia and oxygen in the vapor phase in contact with a catalyst material as described herein.

In another aspect, the disclosure provides a process for the conversion of propylene, isobutylene, or a mixture thereof to acrolein, methacrolein, or a mixture thereof, the process including reacting the propylene, isobutylene, or the mixture thereof with oxygen in the vapor phase in contact with a catalyst material as described herein.

In another aspect, the disclosure provides a metal oxide catalyst having the formula $Mo_xBi_yFe_zNi_aCe_{b1}Mg_{b2}Mn_{b3}K_{d1}Cs_{d2}O_y$, in which x is in the range of 12 to 14, y is in the range of 0.05 to 0.4, z is in the range of 1 to 2.5, a is in the range of 5 to 7, b1 is in the range of 0.2 to 0.6, b2 is in the range of 1 to 3, b3 is in the range of 0.1 to 1.0, d1 is in the range of 0.01 to 0.15, and d2 is in the range of 0.01 to 0.8, for example made by the processes described herein.

BRIEF DESCRIPTION OF THE DRAWINGS

The accompanying drawings are included to provide a further understanding of the methods and devices of the disclosure, and are incorporated in and constitute a part of this specification. The drawings are not necessarily to scale, and sizes of various elements may be distorted for clarity. The drawings illustrate one or more embodiment(s) of the disclosure, and together with the description serve to explain the principles and operation of the disclosure.

DETAILED DESCRIPTION

Figure 1:
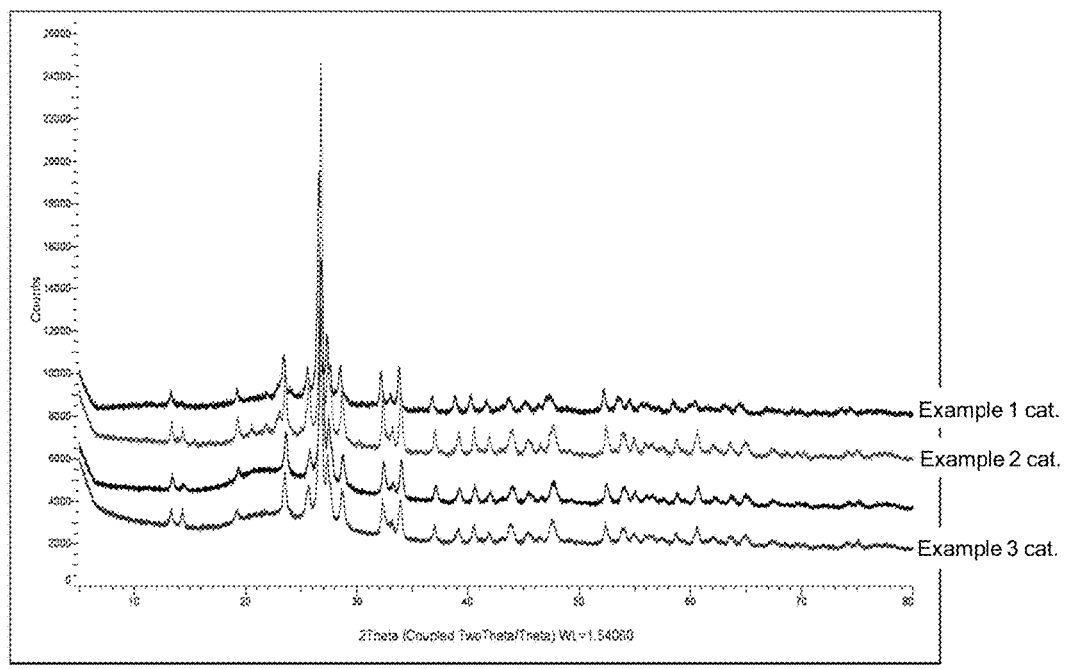
FIG. 1 illustrates X-ray diffraction (XRD) patterns for the catalysts prepared in Examples 1-3.

Before the disclosed processes and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the term "contacting" includes the physical contact of at least one substance to another substance.

All percentages, ratios and proportions herein are by weight, unless otherwise specified. A weight percent (weight %, also as wt %) of a component, unless specifically stated to the contrary, is based on the total weight of the formulation or composition in which the component is included (e.g., on the total amount of the catalyst material). All mol % values are based on the moles of metal atoms.

In view of the present disclosure, the processes and active materials described herein can be configured by the person of ordinary skill in the art to meet the desired need. In general, the disclosed materials, methods, and apparati provide improvements in processes for preparing highly efficient catalyst suitable for partial oxidation and/or ammoxidation of olefins, such as propylene or isobutylene. The processes of the disclosure are simple and cost-efficient, and can eliminate or reduce the need for the binders or additives typically used in impregnation methods. The inventors have determined that combining the inert carrier with the metal oxide precursor fluid with certain metal oxide precursors thereof in a substantially dissolved state can provide catalyst materials having improved catalytic effectiveness. For example, the inventors have determined that a molybdenum oxide precursor can be combined with one or more of bismuth oxide precursor and iron oxide precursor such that substantially no, or relatively little precipitate is formed, such that the precursors do not form a slurry or a gel in the metal oxide precursor fluid. As a result, the catalysts prepared by the processes of the disclosure can have a more uniform distribution of the catalytically active component in the form of a thin layer on the surface of the support that allows for the catalytically active component to be available for the oxidation reaction. The catalysts prepared by the processes of the disclosure can also have improved mechanical strength. In addition, unlike the conventionally prepared catalysts, the catalysts prepared by the processes of the disclosure do not contain substantial amounts of $Fe_2(MoO_4)_3$; rather, the molybdenum can be substantially in the form of crystalline $\alpha$-$NiMoO_4$ and $\beta$-$NiMoa_4$.

Thus, one aspect of the disclosure is a process for making a catalyst material. The catalyst material includes an inert carrier in an amount in the range of about 25 wt % to about 75 wt %. The catalyst material also includes a metal oxide catalyst (for example, a molybdenum-containing mixed metal oxide, e.g., of the formula $Mo_xBi_yFe_zA_aB_bC_cD_dO_v$) in an amount in the range of about 25 wt % to about 75 wt %. As the person of ordinary skill in the art will appreciate, the catalyst material itself will be formed as a fused composite of inert carrier particles and metal oxide particles. As described in further detail below, the metal oxide can be, for example, a molybdenum-containing mixed metal oxide (e.g., of the formula $Mo_xBi_yFe_zA_aB_bC_cD_dO_v$) suitable for use as an ammoxidation catalyst in the synthesis of acrylonitrile or methacrylonitrile or as a partial oxidation catalyst for the synthesis of acrolein or methacrolein.

In certain aspects of the disclosure, the process includes providing a metal oxide precursor fluid comprising a solvent in admixture with a plurality of metal oxide precursors, the plurality of metal oxide precursors comprising at least a molybdenum oxide precursor, a bismuth oxide precursor, and an iron oxide precursor. The metal oxide precursor fluid, optionally combined with the inert carrier, if used, is spray-dried and calcined to form the catalyst material.

As used herein, a "metal oxide precursor" is any species that is or results in a metal oxide species in the final catalyst, e.g., chemical compounds comprising metals and/or metalloids, which produce an effect in the reaction to be catalyzed by the catalyst material and which can form metal oxide upon calcination. This can include, for example, the raw materials as metal feedstocks (e.g., in the form of nitrates, sulfates, acetates, etc.). But the term "precursor" can also include any compound formed from such feedstocks, e.g., in the metal oxide precursor fluid, as a reaction product of other metal oxide precursors. And the person of ordinary skill in the art will appreciate that the term "metal oxide" includes not only compounds of the form $MO_x$ but also of the form $M^1_y(M^2O_x)_z$. As is common in the art, in the final catalyst material these are all considered together as part of the mixed metal oxide.

In certain embodiments of the processes described herein, each of the molybdenum oxide precursor, the bismuth oxide precursor, and the iron oxide precursor is essentially completely dissolved in the solvent, e.g., by having at least 99% by weight of each metal oxide precursor being dissolved in solution. The term "essentially completely dissolved" means that at least 99% by weight, of the metal oxide precursor is dissolved in the solution. Desirably, the metal oxide precursor fluid of such embodiments is substantially free of residues, apart from technically unavoidable impurities, and thus is a clear solution and not be a slurry, gel, suspension, or other type of dispersion (e.g., of one or more of the described metal oxide precursors, or, in some embodiments, of all of the metal oxide precursors). Accordingly, the person of ordinary skill in the art will select reagents and conditions, based on the disclosure herein, where relatively little of the metal species precipitate, or react to form insoluble product in the metal oxide precursor fluid.

In certain embodiments of the processes described herein, less than about 20 wt % of each of the molybdenum oxide precursor, the bismuth oxide precursor, and the iron oxide precursor is not dissolved in the solvent of the precursor fluid. The amounts are calculated on a metal oxide basis (e.g., each metal being taken as its simple oxide). For example, in certain embodiments, less than about 15 wt %, or less than about 10 wt %, or less than about 7 wt %, or less than about 5 wt %, or less than about 2 wt %, or less than about 1 wt % of each of the molybdenum oxide precursor, the bismuth oxide precursor, and the iron oxide precursor is not dissolved in the solvent of the precursor fluid.

The present inventors have determined that, while absolutely complete dissolution of the molybdenum oxide precursor, the bismuth precursor, and the iron oxide precursor can be desirable in certain situations, complete dissolution can be time-consuming and require large volumes of solvent and long times. And in some cases, a small amount of material may precipitate in the metal oxide precursor fluid as a result of reactions between feedstocks. The inventors have noted that metal oxide precursor fluids with small amounts of undissolved material can nonetheless provide acceptable materials for use as catalyst materials. Accordingly, in certain aspects of the disclosure, one or more of the molybdenum oxide precursor, the bismuth precursor, and the iron oxide precursor are not completely dissolved in the metal oxide precursor fluid. Accordingly, in certain embodiments of the processes described herein, between about 0.01 wt % and about 20 wt % of one or more of the molybdenum oxide precursor, the bismuth oxide precursor, and the iron oxide precursor is not dissolved in the solvent. For example, in various particular embodiments of the processes described herein, between about 0.01 wt % and about 15 wt %, or about 0.01 wt % and about 10 wt %, or about 0.01 wt % and about 5 wt %, or about 0.01 wt % and about 5 wt %, or about 0.01 wt % and about 3 wt %, or about 0.01 wt % and about 2 wt %, or about 0.01 wt % and about 1 wt %, or about 0.1 wt % and about 20 wt %, or about 0.1 wt % and about 15 wt %, or about 0.1 wt % and about 10 wt %, or about 0.1 wt % and about 5 wt %, or about 0.1 wt % and about 5 wt %, or about 0.1 wt % and about 3 wt %, or about 0.1 wt % and about 2 wt %, or about 0.1 wt % and about 1 wt %, or about 1 wt % and about 20 wt %, or about 1 wt % and about 15 wt %, or about 1 wt % and about 10 wt %, or about 1 wt % and about 5 wt %, or about 1 wt % and about 5 wt %, or about 1 wt % and about 3 wt %, or about 1 wt % and about 2 wt % of one or more of (e.g., each of) the molybdenum oxide precursor, the bismuth oxide precursor, and the iron oxide precursor is not dissolved in the solvent.

For example, in certain embodiments of the processes described herein, a portion of each of the molybdenum oxide precursor and the bismuth oxide precursor is not dissolved in the solvent, e.g., in an amount as described above. In other embodiments of the processes described herein, a portion of each of the molybdenum oxide precursor and the iron oxide precursor is not dissolved in the solvent, e.g., in an amount as described above. In other embodiments of the processes described herein, a portion of each of the bismuth oxide precursor and the iron oxide precursor is not dissolved in the solvent, e.g., in an amount as described above. In certain embodiments of the processes described herein, a portion of each of the molybdenum oxide precursor, the bismuth oxide precursor, and the iron oxide precursor is not dissolved in the solvent, e.g., in an amount as described above.

The metal oxide precursor fluid can include a variety of other metal oxide precursors, e.g., to provide the overall mixed metal oxide catalyst composition desired. Each of these precursors can be, for example, essentially completely dissolved in the metal oxide precursor fluid, or, as one alternative, can remain partially undissolved, e.g., in an amount as described above.

As described above, the processes described herein involve the provision of a metal oxide precursor fluid. The metal oxide fluid comprises a solvent in admixture with a plurality of metal oxide precursors. The individual metal oxide precursor compounds may be dissolved in a suitable solvent, and/or commercially available, ready-to-use solutions of the individual metal oxide precursors may be used. In one embodiment, all metal oxide precursors necessary for producing the catalyst material are in admixture with the solvent. In certain embodiments, providing a metal oxide precursor fluid comprises: dissolving molybdenum oxide precursor and bismuth oxide precursor in the solvent to obtain a solution (i.e., optionally with some undissolved material as described above); and adding the iron oxide precursor to the clear solution. In certain embodiments, providing a metal oxide precursor fluid comprises: dissolving molybdenum oxide precursor and bismuth oxide precursor in the solvent to obtain a solution (i.e., optionally with some undissolved material as described above); and adding the iron oxide precursor and one or more metal oxide precursors to the clear solution.

Because the effective forms of the catalytically active metals and/or metalloids are frequently sparingly soluble, soluble forms of the corresponding metals and/or metalloids, in particular slightly soluble metal salts and/or metalloid salts, may be used as the metal oxide precursor compounds. Thus in certain embodiments, the metal oxide precursors are provided as salts. These salts, for example, may be any suitable salts as long as they are soluble in a suitable solvent. For example, each precursor material may be a water soluble metal salt such as, but not limited to, a metal nitrate, a metal sulfate, a metal halide, or a metal acetate; certain precursor materials may be provided with the metal species in the anion (e.g. oxide anions of molybdenum, manganese, chromium, tungsten or vanadium). In certain embodiments of the processes of the disclosure, the divalent and trivalent metal oxide precursors are provided as nitrate salts, acetate salts, or combinations thereof. In certain embodiments of the processes of the disclosure, the divalent and trivalent metal oxide precursors are provided as acetate salts. In certain embodiments of the processes of the disclosure, the divalent and trivalent metal oxide precursors are provided as nitrate salts.

Non-limiting examples of suitable molybdenum metal oxide precursors include molybdates, such as heptamolybdates ($Mo_7O_{24}^{6-}$). In one embodiment, the molybdenum metal oxide precursor is ammonium heptamolybdate (e.g., ammonium heptamolybdate tetrahydrate). Non-limiting examples of suitable bismuth metal oxide precursors include inorganic or organic salts of bismuth, in particular bismuth nitrate, bismuth subsalicylate, or bismuth citrate. In one embodiment, the bismuth metal oxide precursor is bismuth nitrate. Non-limiting examples of suitable iron metal oxide precursors include inorganic or organic salts of iron(III), in particular iron(III) nitrate, iron(III) salicylate, or iron(III) citrate. In one embodiment, the iron metal oxide precursor is iron(III) nitrate. Non-limiting examples of suitable nickel metal oxide precursors include nickel acetate, nickel nitrate, nickel salicylate, or nickel citrate. In one embodiment, the nickel metal oxide precursor is nickel acetate. Non-limiting examples of suitable cobalt metal oxide precursors include cobalt acetate, cobalt nitrate, cobalt salicylate, or cobalt citrate. In one embodiment, the cobalt metal oxide precursor is cobalt acetate. Non-limiting examples of suitable magnesium metal oxide precursors include magnesium acetate, magnesium nitrate, magnesium salicylate, or magnesium citrate. In one embodiment, the magnesium metal oxide precursor is magnesium acetate. Non-limiting examples of suitable manganese metal oxide precursors include manganese acetate, manganese nitrate, or manganese citrate. In one embodiment, the manganese metal oxide precursor is manganese acetate. Non-limiting examples of suitable tungsten metal oxide precursors include tungstates, in particular ammonium tungstates. In one embodiment, the tungsten metal oxide precursor is ammonium metatungstate. Non-limiting examples of suitable potassium metal oxide precursors include potassium acetate, potassium nitrate, potassium salicylate, or potassium citrate. In one embodiment, the potassium metal oxide precursor is potassium acetate. Non-limiting examples of suitable cesium metal oxide precursors include cesium acetate, cesium nitrate, cesium salicylate, or cesium citrate. In one embodiment, the cesium metal oxide precursor is cesium acetate. Other suitable salts of the above-mentioned metals as well as salts of other metals, for example chromium, zinc, cerium, calcium, and/or of metalloids may be easily selected by those skilled in the art. Mixtures of various salts of the same metal may also be used.

In certain embodiments of the disclosure, the counterion of the salts of the metal oxide precursors may be removed with essentially no residues in the heating of the processes of the disclosure.

As noted above, a suitable solvent is used to provide the metal oxide precursor fluid. In one embodiment, the suitable solvent is an aqueous solvent, i.e., a solvent composed of water, or a solvent mixture which in addition to water contains one or more further solvents that are miscible with water, such as polar organic solvents, such as alcohols. The use of an aqueous solvent is economically and environmentally advantageous.

In certain embodiments, the aqueous solvent is an acidic aqueous solvent, by means of which the substantial dissolution of the precursor compounds of the catalytically active component is facilitated in many cases. This is specifically advantageous in that bismuth oxide precursors and molybdenum oxide precursors are usually not soluble in one solution under the same conditions. Acidifying the aqueous solvent is not subject to any special limitations as long as it is suitable for substantially dissolving the precursor compounds, and as long as it does not impair the catalytic activity of the finished catalyst. Use of an acidic aqueous solvent also results in very low particle growth that provides a relatively high Brunauer-Emmett-Teller (BET) Surface Area for the particles. Another advantage of using an acidic aqueous solvent is that the metal oxide fluid can be provided as a substantially homogeneous solution of the metal oxide precursors (i.e., with little or no undissolved material therein), which in turn provides that substantially all of the catalytically active components are evenly distributed over the entire catalyst. It is more difficult to achieve substantially complete dissolution in the absence of acid.

The acidic aqueous solvent may include inorganic or organic acids. Organic acids suitable in the processes of the disclosure include, but are not limited to, glycolic acid, acetic acid, lactic acid, citric acid, oxalic acid, malonic acid, succinic acid, adipic acid, maleic acid, tartaric acid, or mixtures thereof. In some embodiments, the organic acid is a chelating organic acid, i.e. be capable to stabilize the metals of the precursor compounds of the catalytically active component by means of more than one coordinative bond. These chelating organic acids are preferably α-hydroxycarboxylic acids or dicarboxylic acids. An advantageous pH of the acidic aqueous solvent is in the range of pH 0 to 6, or pH 0.5 to 4. A suitable pH may be easily selected by those skilled in the art, taking into account the particular precursor compounds of the catalytically active component to be used. In one embodiment of the processes of the disclosure, the solvent is an organic solvent; or the acidic solvent is an aqueous solution of glycolic acid, acetic acid, lactic acid, citric acid, oxalic acid, malonic acid, succinic acid, adipic acid, maleic acid, tartaric acid, or mixtures thereof, or the solvent is an aqueous solution of glycolic acid, acetic acid, lactic acid, or mixtures thereof; or the solvent is an aqueous solution of glycolic acid. The acidic aqueous solvent can have a relatively high amount of acid, e.g., in the range of 45-90 wt %, or 55-90 wt %, or 45-80 wt %, or 55-80 wt %, or 65-90 wt %, or 65-85 wt % acid. The acid can be present in the metal oxide precursor fluid in an amount, for example, such that the molar ratio of acid to metal is at least 1, e.g., in the range of 1-3, or in the range of 1-2, or in the range of 1-1.5.

In certain processes of the disclosure, the metal oxide precursor fluid is brought into contact with an inert carrier. The inert carrier has a specific surface of 1 to 500 m$^2$/g (measured according to the BET method of DIN ISO 9277: 2010 or DIN 66134). The term "inert" as used herein means chemically inert during the reaction to be catalyzed by the catalyst, i.e., the inert carrier material does not take part in a chemical reaction, in particular with substances participating in the reaction to be catalyzed. In one embodiment of the processes of the disclosure, the inert carrier is an inorganic support material. Suitable examples include, but are not limited to, silicon carbide, silicon dioxide, zirconium dioxide, titanium dioxide, aluminum oxide, niobium pentoxide, hafnium dioxide, tantalum pentoxide, antimony tetroxide, porous ceramics, sheet silicates, bentonites, and mixtures thereof. Supports that are not inorganic, in particular carbon-based supports, may also be used. In certain embodiments, the inert carrier is selected from $SiO_2$, $Al_2O_3$, $ZrO_2$, $Nb_2O_5$, $TiO_2$, $HfO_2$, $Ta_2O_5$, $Sb_2O_5$, and their mixed oxides. In certain embodiments, the inert carrier is silica. The inert carrier can be in any desirable form, e.g., in particulate form (e.g., for use as a fluid bed catalyst) or in the form of larger pieces of material (e.g., in the form of spheres, pellets, cylinders (hollow or otherwise), symmetrical or asymmetrical tri-quadrulobes) for use as a fixed bed catalyst, In certain embodiments, and especially when the catalyst material is made by spray-drying, the inert carrier is desirably provided with a relatively small average particle size, e.g. less than about 10 microns, or less than about about 1 micron, or less than about 500 nm, or less than about 100 nm. For example, the average particle size of the inert carrier can be in the range of 1 nm-100 nm. In certain embodiments, the inert carrier is nanoparticulate silica, e.g., provided as colloidal silica or fumed silica, or a combination of the two.

As described above, the metal oxide precursor fluid can have particles of the inert carrier suspended therein to form a suspension or slurry. The suspension or slurry can be spray-dried to produce a spray-died precursor material. Any suitable spray-drying methods know in the art may be used. In general, the suspension or slurry may be atomized and introduced into a stream of heated, drying gas such as air, nitrogen, argon, and the like, or any combination thereof to evaporate the solvent and produce solid-form particles of the spray-dried precursor material. The volumetric flow of the drying gas can be greater than the volumetric flow of the suspension or slurry. The suspension or slurry can be atomized using any suitable device(s), system(s), or combination of device(s) and/or system(s). For example, the suspension or slurry can be atomized via an atomizing nozzle or a centrifugal high speed disc atomizer. Atomization of the suspension or slurry via an atomizing nozzle can also include mixing the suspension or slurry with an atomizing gas. The temperature of the atomizing nozzle can be at or above the boiling point of the highest boiling component of the suspension or slurry. The atomized suspension or slurry can be introduced to a drying chamber where the volatiles can dry in the presence of the heated, drying gas. Other suitable spray-dry processes can be similar to those discussed and described in, for example, U.S. Pat. Nos. 4,638,029, 4,728,705, 5,290,745, 5,306,350, 5,604,172, 5,716,558, and 6,982,236.

The spray-died precursor material can then undergo heating, so that the metal oxide precursor compounds are decomposed into their oxides (i.e. the catalytically active component). In one embodiment, heating includes calcination. The term "calcination" is generally understood to mean heating to high temperatures with the objective of changing, in particular materially or structurally, the treated material or a component thereof. As the result of calcination, for example thermal decomposition, a phase transition, or the removal of volatile substances may be achieved. In the processes of the invention, in particular, the metal oxide precursors, which have been used to form the metal oxide precursor fluid as stated above, are decomposed into their respective oxides, i.e., converted to their catalytically effective form. In one embodiment, the calcination is at a temperature of about 200 to 700° C., or about 250° C. to about 650° C., or about 450° C. to about 650° C., or about 600° C. to about 650° C., or about 500 to about 610° C. In one embodiment, the calcination is performed at two temperatures where the first temperature is at about 200° C. to about 300° C. and the second temperature is at about 450° C. to about 650° C. In one embodiment, the calcination is performed at two temperatures where the first temperature is at about 250° C. to about 300° C. and the second temperature is at about 600° C. to about 650° C. The duration of the calcination is between about 30 min to about 20 h, or about 30 min to about 15 h, or about 30 min to 10 h, or about 30 min to 1 h, or about 45 min to 1 h.

The catalyst material obtained by the processes of the disclosure may be provided in any suitable form. In certain embodiments, the catalyst material is provided as a plurality of discrete particles, as is common for catalysts to be used in fluidized bed applications. The discrete particles can be formed in a variety of particle sizes and distributions. The discrete particles can be, for example, substantially spheroidal in shape, as would result from a spray drying process. The person of ordinary skill in the art can tune the spray drying process (or other processes) to provide the desired particle shape and size. Catalyst materials useful for fluid bed processes can have medial particle sizes ranging, for example, in the range of 10 μm to 1 mm. Of course, in other embodiments, the catalyst material can be formed in other shapes. For example, the spray-dried catalyst material can be formed into shapes such as spheres, pellets, cylinders (hollow or otherwise), symmetrical or asymmetrical tri-quadrulobes, for example, using extrusion or tableting methods. Such catalyst materials may be suitable for use in fixed bed reactors, for example, when having a median maximum dimension in the range of 2 mm to 20 mm. Catalyst materials may also be coated on to a substrate or support, such as a ceramic surface or an internal surface of a reactor.

As described above, the catalyst materials prepared by the processes of the disclosure include a metal oxide catalyst in an amount in the range of about 25 wt % to about 75 wt %. For example, in certain embodiments, the metal oxide catalyst is present in an amount in the range of about 30 wt % to about 70 wt %. In other embodiments, the metal oxide catalyst is present in an amount in the range of about 35 wt % to about 65 wt %, or about 40 wt % to about 60 wt %, or about 45 wt % to about 55 wt %, or about 25 wt % to about 65 wt %, or about 25 wt % to about 55 wt %, or about 35 wt % to about 55 wt %, or about 35 wt % to about 75 wt %, or about 45 wt % to about 75 wt %, or about 45 wt % to about 65 wt %. For example, in certain embodiments, the metal oxide catalyst is present in an amount of about 50 wt % of the catalyst material.

The catalyst material can in some embodiments include other materials. However, in certain particularly advantageous embodiments, the inert carrier and the metal oxide catalyst are together present in the catalyst material in an amount of at least about 80 wt %, or at least about 90 wt %, or at least about 95 wt %, or at least about 98 wt %, or at least about 99 wt %, or at least about 99.5 wt %, or even at least about 99.9 wt %. For example, in certain embodiments, the catalyst material consists essentially of the inert carrier and the metal oxide catalyst.

A number of metal oxide catalysts can be used. For example, in certain embodiments, the metal oxide catalyst is a mixed metal oxide catalyst, for example, a mixed metal oxide ammoxidation catalyst suitable for the conversion of propylene to acrylonitrile and/or isobutylene to methacrylonitrile, and/or for the for the conversion of propylene to acrolein and/or isobutylene to methacrolein. The mixed metal oxide catalyst can, for example, be a molybdenum-containing mixed metal oxide.

As described above, the catalyst materials of the disclosure can in certain embodiments include as the metal oxide catalyst a mixed metal oxide of the formula $Mo_xBi_yFe_zA_aB_bC_cD_dO_v$, in an amount in the range of about 25 wt % to about 75 wt %. In such embodiments x is in the range of 10 to 14; y is in the range of 0.05 to 5; z is in the range of 0.2 to 5; A is at least one element selected from Ni and Co; a is in the range of 1 to 10; B is at least one element selected from the lanthanides, Mg, Cr, Mn, Zn and Ca; b is in the range of 0.01 to 6; C is at least one element selected from Sn, V, Ti, Zr, Ga, Hf, Nb, Ta, In and Al; c is in the range of 0 to 8; D is at least one element selected from Li, Na, K, Rb and Cs; d is in the range of 0.02 to 2; and v is the number of oxygen atoms required to satisfy the valence requirements of the other component elements Mo, Bi, Fe, A, B, C, and D. The person of ordinary skill in the art will appreciate that the formulae described herein merely refer to the relative amounts of the various constituents. For example, a material having the formula $Mo_6BiFeA_{0.5}B_{0.5}D_{0.5}O_{2v}$ would also be understood to have the formula $Mo_{12}Bi_2Fe_2ABDO_v$. The stoichiometry of the mixed metal oxide is determined on a dry basis, i.e., discounting any adsorbed water.

As the person of ordinary skill in the art will appreciate, the metal oxide catalyst may be provided in many forms and morphologies. It may include crystalline regions, amorphous regions, or a combination of the two. Moreover, the metal oxide need not be substantially homogeneous; there may be regions of the metal oxide that have varying compositions as compared to the rest of the metal oxide. As the person of ordinary skill in the art will appreciate, the disclosed formula $Mo_xBi_yFe_zA_aB_bC_cD_dO_v$ (or any other formula disclosed herein) represents the average composition of the metal oxide. When A comprises more than one metal, the sum of molar fractions of those metals result in coefficient a. When B comprises more than one metal, the sum of the molar fractions of those metals result in coefficient b. When C comprises more than one metal, the sum of molar fractions of those metals result in coefficient c. When D comprises more than one metal, the sum of molar fractions of those metals result in coefficient d.

As described above, the coefficient x in the formula $Mo_xBi_yFe_zA_aB_bC_cD_dO_v$ in the catalyst materials of the disclosure is in the range of 10-14. For example, in various particular embodiments of the catalyst materials as described herein, x is in the range of 11-14 or in the range of 11-13. In certain embodiments, x is 12. In certain embodiments, x is 13.

As described above, the coefficient y in the formula $Mo_xBi_yFe_zA_aB_bC_cD_dO_v$ is in the range of 0.05 to 5. For example, in various particular embodiments of the catalyst materials as described herein, y is in the range of 0.05 to 3, or 0.05 to 2, 0.05 to 1, or 0.05 to 0.5, or 0.05 to 0.35, or 0.1 to 5, or 0.1 to 3, or 0.1 to 2, or 0.1 to 1, or 0.1 to 0.5, or 0.1 to 0.35, or 01.5 to 5, or 0.15 to 3, or 0.15 to 2, or 0.15 to 1, or 0.15 to 0.5, or 0.15 to 0.35, or 0.2 to 5, or 0.2 to 3, or 0.2 to 2, or 0.2 to 1, or 0.2 to 0.5, or 0.2 to 0.35, or 0.5 to 5, or 0.5 to 2, or 0.7 to 1.5, or 0.8 to 1.4, or 0.9 to 1.3, or 1.0 to 1.2.

As described above, the coefficient z in the formula $Mo_xBi_yFe_zA_aB_bC_cD_dO_v$ is in the range of 0.2 to 5. For example, in various particular embodiments of the catalyst materials as described herein, z is in the range of 0.2 to 4, or 0.2 to 3, or 0.2 to 2, or 0.5 to 5, or 0.5 to 4, or 0.5 to 3, or 0.5 to 2, or 1 to 5, or 1 to 4, or 1 to 3, or 1 to 2, or 1.5 to 5, or 1.5 to 4, or 1.5 to 3, or 1.5 to 2, or 1.1 to 5, or 1.1 to 4, or 1.1 to 3, or 1.1 to 2, or 1.2 to 5, or 1.2 to 4, or 1.2 to 3, or 1.2 to 2 or 1.1 to 1.3.

As described above, A in the formula $Mo_xBi_yFe_zA_aB_bC_cD_dO_v$ is at least one element selected from Ni and Co. For example, in various particular embodiments of the catalyst materials as described herein, A is Ni. In other embodiments, A is Co. In still other embodiments, A is a combination of Ni and Co.

As described above, the coefficient a in the formula $Mo_xBi_yFe_zA_aB_bC_cD_dO_v$ is in the range of 1 to 10. For example, in various particular embodiments of the catalyst materials as described herein, a is in the range of 1 to 8, or 1 to 7, or 1 to 6.7, or 2 to 10, or 2 to 8, or 2 to 7, or 2 to 6.7, or 3.5 to 10, or 3.5 to 8, or 3.5 to 7, or 3 to 6.7, or 4.5 to 10, or 4.5 to 8, or 4.5 to 7, or 4 to 6.7, or 5 to 7, or 6 to 6.7, or 6.3 to 6.7.

As described above, B in the formula $Mo_xBi_yFe_zA_aB_bC_cD_dO_v$ is at least one element selected from the lanthanides, Mg, Cr, Mn, Zn and Ca. For example, in various particular embodiments of the catalyst materials as described herein, B is at least one element selected from Ce, Mg, Cr, Mn, Zn and Ca. In other embodiments, B is at least one element selected from Ce, Mg, Cr and Mn. For example, B can include each of Ce, Mg, Cr and Mn; or B can include each of Ce, Mg, and Mn.

As described above, the coefficient b in the formula $Mo_xBi_yFe_zA_aB_bC_cD_dO_v$ is in the range of 0.01 to 6 For example, in various particular embodiments of the catalyst materials as described herein, b is in the range of 0.01 to 5, or 0.01 to 4, or 0.01 to 3.5, or 0.01 to 2, or 0.01 to 1, or 0.01 to 0.5, or 0.05 to 6, or 0.05 to 5, or 0.05 to 4, or 0.05 to 3.5, or 0.05 to 2, or 0.05 to 1, or 0.05 to 0.5, or 0.1 to 6, or 0.1 to 5, or 0.1 to 4, or 0.1 to 3.5, or 0.5 to 6, or 0.5 to 5, or 0.5 to 4, or 0.5 to 3.5, or 1 to 6, or 1 to 5, or 1 to 4, or 1 to 3.5, or 2 to 6, or 2 to 5, or 2 to 4, or 2 to 3.5, or 3 to 6, or 3 to 5, or 3 to 4, or 3 to 3.5.

As described above, C is at least one element selected from W, Sn, V, Ti, Zr, Ga, Hf, Nb, Ta, In and Al. In certain embodiments, C is at least one element selected from Sn, V, Ti, Zr, Ga, Hf, Nb, Ta, In and Al. In certain embodiments, C is at least one element selected from Sn, V, Ti, Zr, Ga, In and Al. In certain embodiments, C is at least one element selected from W, Sn, V, Ti and Zr. In other embodiments, C is at least one element selected from W, Sn and V. In one embodiment, C is W. In other embodiments, C does not include W.

As described above, c is in the range of 0 to 8. In certain embodiments, the mixed metal oxide is substantially free of W, Sn, V, Ti, Zr, Ga, Hf, Nb, Ta, In and Al. Accordingly, in certain embodiments, c is substantially zero. In other embodiments, c is in the range of 0 to 6, or 0 to 4, or 0 to 2, or 0 to 1, or 0 to 0.5, or 0 to 0.2, or 0 to 0.1, or 0.05 to 8, or 0.05 to 6, or 0.05 to 4, or 0.05 to 2, or 0.05 to 1, or 0.05 to 0.5, or 0.05 to 0.2, or 0.05 to 0.1, or 0.1 to 8, or 0.1 to 6, or 0.1 to 4, or 0.1 to 2, or 0.1 to 1, or 0.1 to 0.5, or 0.1 to 0.2.

As described above, D is at least one element selected from Li, Na, K, Rb and Cs. For example, in various particular embodiments of the catalyst materials as described herein, D is at least one element selected from Li, Na, K and Cs. In one embodiment, D is at least one element selected from Li, K and Cs, or selected from K and Cs. In certain embodiments, D is a combination of K and Cs.

As described above, d is in the range of 0.02 to 2. For example, in various particular embodiments of the catalyst materials as described herein, d is in the range of 0.02 to 1, or 0.02 to 0.5, or 0.02 to 0.2, or 0.05 to 2, or 0.05 to 1, or 0.05 to 0.5, or 0.05 to 0.2, or 0.1 to 2, or 0.1 to 1, or 0.1 to 0.5, or 0.1 to 0.2.

As described above, v is the number of oxygen atoms required to satisfy the valence requirements of the other component elements Mo, Bi, Fe, A, B, C, and D. The person of ordinary skill in the art will appreciate that the value of y will vary depending on the identities and oxidation states of the various component elements Mo, Bi, Fe, A, B, C, and D.

The person of ordinary skill in the art will select suitable identities of the metal oxide catalyst (e.g., of the component elements Mo, Bi, Fe, A, B, C, and D and values of the various coefficients of the metal oxide) based on the state of the art (e.g., the ammoxidation catalyst art), for example, as described in any of U.S. Pat. Nos. 4,766,232, 4,377,534, 4,040,978, 4,168,246, 4,863,891, 5,093,299, 5,212,137, 5,223,469, 5,658,842, 5,663,112, 5,870,664, 7,473,666 and 7,576,232, and International Patent Application Publication no. WO 2014/169163, each of which is hereby incorporated herein by reference in its entirety.

For example, in certain embodiments, the metal oxide catalyst has the formula $Mo_xBi_yFe_zNi_aCe_{b1}Mg_{b2}Mn_{b3}K_{d1}Cs_{d2}O_y$, in which x is in the range of 12 to 14, y is in the range of 0.05 to 0.4, z is in the range of 1 to 2.5, a is in the range of 5 to 7, b1 is in the range of 0.2 to 0.6, b2 is in the range of 1 to 3, b3 is in the range of 0.1 to 1.0, d1 is in the range of 0.01 to 0.15, and d2 is in the range of 0.01 to 0.8.

Indeed, another aspect of the disclosure is a mixed metal oxide catalyst material having the formula $Mo_xBi_yFe_zNi_aCe_{b1}Mg_{b2}Mn_{b3}K_{d1}Cs_{d2}O_y$, in which x is in the range of 12 to 14, y is in the range of 0.05 to 0.4, z is in the range of 1 to 2.5, a is in the range of 5 to 7, b1 is in the range of 0.2 to 0.6, b2 is in the range of 1 to 3, b3 is in the range of 0.1 to 1.0, d1 is in the range of 0.01 to 0.15, and d2 is in the range of 0.01 to 0.8. The mixed metal oxide can be supported, for example, on an chemically inert carrier, such as, for example, silicon carbide, silicon dioxide, zirconium dioxide, titanium dioxide, aluminum oxides, porous ceramics, sheet silicates, bentonites and mixtures thereof. Such a catalyst material can include, for example, in the range of about 25 wt % to about 75 wt % of the carrier, and in the range of about 25 wt % to about 75 wt % mixed metal oxide.

Notably, the processes described herein can be used to provide materials with a more desirable distribution of pore sizes. For example, in certain embodiments, the catalyst material has a cumulative volume of pores having a pore size in the range of 1000 Å to 5000 Å that is in the range of about 0.1% to about 20%, or about 0.1% to about 10%, or about 0.5% to about 20%, or about 0.5% to about 10%, or about 1% to about 20%, or about 1% to about 10% of the total volume of pores having sizes in the range of 1000 Å to 5000 Å.

The catalyst materials described herein can be provided with a variety of different pore volumes. For example, in certain embodiments, a catalyst material as described herein has a pore volume of about 0.05 to about 1.5 $cm^3/g$, or about 0.1 to about 1.5 $cm^3/g$, or about 0.5 to about 1.5 $cm^3/g$, or about 0.1 to about 1 $cm^3/g$, or about 0.2 to about 1 $cm^3/g$, or about 0.3 to about 1 $cm^3/g$, or about 0.5 to about 1 $cm^3/g$, or 0.05 to about 0.5 $cm^3/g$, or about 0.1 to about 0.5 $cm^3/g$, or about 0.2 to about 0.5 $cm^3/g$, or 0.1 to about 0.7 $cm^3/g$, or about 0.2 to about 0.7 $cm^3/g$, or about 0.4 to about 0.7 $cm^3/g$; or more than about 0.3 $cm^3/g$, or more than about 0.4 $cm^3/g$, or more than about 0.5 $cm^3/g$, or more than about 0.6 $cm^3/g$. The person of ordinary skill in the art can, in view of the processes described herein, provide a desired pore volume to a catalyst material. Pore volumes are measured by Hg porisometry, and provide the total volume or pores below 5000 Å in size.

Similarly, the catalyst materials described herein can be provided with a variety of different surface areas, depending, e.g., on the processes used for making them and the desired end use. The surface areas are measured using the Brunauer-Emmett-Teller (BET) Surface Area method. In certain embodiments, a catalyst material as described herein has a surface area within the range of from about 10 to about 400 $m^2/g$, or about 50 to about 400 $m^2/g$, or about 70 to about 400 $m^2/g$, or about 100 to about 400 $m^2/g$, or about 200 to about 400 $m^2/g$, or about 300 to about 400 $m^2/g$, or about 10 to about 300 $m^2/g$, or about 50 to about 300 $m^2/g$, or about 70 to about 300 $m^2/g$, or about 100 to about 300 $m^2/g$, or about 200 to about 300 $m^2/g$, or about 100 to about 250 $m^2/g$, or about 10 to about 200 $m^2/g$, or about 50 to about 200 $m^2/g$, or about 70 to about 200 $m^2/g$, or about 100 to about 200 $m^2/g$, or about 10 to about 100 $m^2/g$, or about 10 to about 80 $m^2/g$, or about 10 to about 60 $m^2/g$, or about 10 to about 50 $m^2/g$, or about 30 to about 100 $m^2/g$, or about 30 to about 80 $m^2/g$, or about 30 to about 60 $m^2/g$, or about 30 to about 50 $m^2/g$, or about 40 to about 50 $m^2/g$. In one embodiment, a catalyst material as described herein has a surface area of about 10 to about 50 $m^2/g$. In another embodiment, a catalyst material as described herein has a surface area of about 40 to about 50 $m^2/g$. The person of ordinary skill in the art can, in view of the processes described herein, provide a desired surface area to a catalyst material.

As used herein, the attrition resistance is measured as the Davison Index (D.I.), which is determined by an attrition index method based on one developed by the Davison Chemical Division of W. R. Grace & Company. The method uses a jet cup attrition technique that reports as the D.I. the wt % of <20 μm fines produced in a controlled attrition test. The D.I. test apparatus consists of two main vessels, the attrition vessel and the elutriation vessel. The attrition and elutriation vessels have diameters of 9 in. and 4.5 in., respectively. Each vessel is 24 in. high and has a cone shaped bottom that slopes about 15° from vertical. The jet cup attritor which holds the sample for attrition attaches to the bottom of the attrition vessel and is 1.03 in. I.D. by 2 in. deep. A 0.0625 in. diameter hole forms the jet that enters the cup's wall horizontally and is tangent to the inside wall and bottom of the cup. A sample 6±0.3 g is attrited for 20 minutes with $N_2$ (35% relative humidity) at a flow rate of about 21 Liters/minute, L/mm (this flow rate is fine-tuned to give a D.I. of 27±2 for a standard CZB-1 Davison catalyst). Fines escaping the attrition vessel are collected in an extraction thimble; their mass is wt1 in the equation below. After the attrition the sample is transferred to the elutriation unit to separate the remainder of the <20 μm fines from the sample. The sample is placed in a cup with similar dimensions than the jet cup but with a sintered metal distributor at the bottom to uniformly fluidize the sample in the elutriator. This cup with the attrited sample is connected to the bottom of the elutriator, and the sample is elutriated for 20 min with $N_2$ (35% relative humidity) at 9 L/min. The elutriation removes the <20 μm fines from the sample to give a remaining coarse fraction (mass is wt3 in the equation below). The elutriated fines (mass is wt2 in the equation below) are collected in an extraction thimble connected to the exit of the elutriation vessel. In a separate measurement, the wt % of <20 μm fines (% PreAtt in the equation below) is determined in a fresh sample (i.e., as described above for the attrited sample). The D.I. represents the wt % of <20 μm fines formed by the attrition, and is calculated using the equation:

$$D.I. = \frac{\frac{wt1 + wt2}{wt1 + wt2 + wt3} \times 100 - (\% \ PreAtt)}{100 - (\% \ PreAtt)} \times 100$$

Advantageously, in certain embodiments, the catalyst materials as described herein have an attrition resistance of less than 1 (i.e., a D.I. of less than 1). In certain embodiments, the catalyst materials as described herein have an attrition resistance of less than 0.6, or less than 0.4, or less than 0.3, or less than 0.2, or less than 0.1. Of course, suitable materials may yet have a nonzero attrition resistance (i.e., measured as D.I.) In some embodiments, the attrition resistance is in the range of 0.05 to 0.6, or 0.05 to 0.4, or 0.05 to 0.3, or 0.05 to 0.2, or 0.05 to 0.1, or 0.1 to 1, or 0.1 to 0.6, or 0.1 to 0.4, or 0.1 to 0.3, or 0.1 to 0.2, or 0.2 to 0.6, or 0.2 to 0.4, or 0.2 to 0.3, or 0.2 to 1, or 0.4 to 1, or 0.6 to 1.

The processes described herein can be especially advantageous in that they can provide materials having a relatively low amount of crystalline $Fe_2(MoO_4)_3$. For example, in certain embodiments of the processes as described herein, of the crystalline content of the catalyst material, no more than 20%, e.g., no more than 10%, no more than 5%, no more than 2%, or even no more than 1% is $Fe_2(MoO_4)_3$.

As noted above, the catalyst materials described herein can be used in the conversion of propylene to acrylonitrile, or isobutylene to methacrylonitrile via ammoxidation. Accordingly, various embodiments of the disclosure provide processes for the conversion of propylene, isobutylene, or a mixture thereof to acrylonitrile, methacrylonitrile, or a mixture thereof, the process including reacting the propylene, isobutylene, or the mixture thereof with ammonia and oxygen in the vapor phase with a catalyst material as described herein. In certain embodiments, the process is performed in a fluid bed reactor, although as the person of ordinary skill in the art will appreciate, other types of reactors can be suitably used.

As noted above, the catalyst materials described herein can be also be used in the conversion of propylene to acrolein, or isobutylene to methacrolein via partial oxidation. Accordingly, various embodiments of the disclosure provide processes for the conversion of propylene, isobutylene, or a mixture thereof to acrolein, methacrolein, or a mixture thereof, the process including reacting the propylene, isobutylene, or the mixture thereof with oxygen in the vapor phase with a catalyst material as described herein. In certain embodiments, the process is performed in a fluid bed reactor, although as the person of ordinary skill in the art will appreciate, other types of reactors can be suitably used.

Conditions for the ammoxidation of propylene to acrylonitrile, or of isobutylene to methacrylonitrile, are well-known in the art. For example, U.S. Pat. Nos. 4,766,232, 4,377,534, 4,040,978, 4,168,246, 4,863,891, 5,093,299, 5,212,137, 5,223,469, 5,658,842, 5,663,112, 5,870,664, 7,473,666 and 7,576,232, each of which is hereby incorporated herein by reference in its entirety, describe a variety of ammoxidation processes.

In certain embodiments, the propylene and/or isobutylene is reacted with ammonia and oxygen in contact with a catalyst material as described herein in a fluid bed at an elevated temperature to produce the acrylonitrile and/or methacrylonitrile. As the person or ordinary skill in the art would appreciate, any convenient source of oxygen may be used; for economic considerations, air is a suitable oxygen-providing gas. The reaction can be carried out, for example, at a temperature in the range of about 260° C. to about 600° C., e.g., 310° C. to 500° C., or 350° C. to 480° C., for a variety of contact times, e.g., in the range of 0.1 to 50 seconds, or about 1 to 15 seconds. The molar ratio of oxygen to propylene/isobutylene in the feed can vary; in certain embodiments, the ratio is in the range of 0.5:1 to 4:1, e.g., 1:1 to 3:1. Similarly, the molar ratio of ammonia to olefin in the feed can vary, e.g., from 0.5:1 to 2:1.

Reaction products may be isolated and purified using conventional methodologies. For example, in one embodiment, the reactor effluent is scrubbed with water or an appropriate solvent to remove the reaction products, which are then purified by distillation. It can also be desirable to isolate and purify certain reaction by-products, such as acetonitrile and HCN; the person of ordinary skill can use conventional methodologies to do so.

As noted above, the catalyst materials described herein can be also be used in the conversion of propylene to acrolein, or isobutylene to methacrolein via partial oxidation. Accordingly, various embodiments of the disclosure provide processes for the conversion of propylene, isobutylene, or a mixture thereof to acrolein, methacrolein, or a mixture thereof, the process including reacting the propylene, isobutylene, or the mixture thereof with oxygen in the vapor phase with a catalyst material as described herein. In certain embodiments, the process is performed in a fluid bed reactor, although as the person of ordinary skill in the art will appreciate, other types of reactors can be suitably used.

Conditions for the partial oxidation of propylene to acrolein, or of isobutylene to methacrolein, are well-known in the art. For example, U.S. Pat. Nos. 6,437,193, 6,462,232, and 8,480,998, International patent Application Publication no. WO 1999/003809 and European Patent Application Publication no. EP 0253409, each of which is hereby incorporated herein by reference in its entirety, describe a variety of oxidation processes.

In certain embodiments, the propylene and/or isobutylene is reacted with oxygen (e.g., in the presence of nitrogen) in contact with a catalyst material as described herein at an elevated temperature to produce the acrylonitrile and/or methacrylonitrile. As the person or ordinary skill in the art would appreciate, any convenient source of oxygen may be used; for economic considerations, air is a suitable oxygen-providing gas. The reaction can be carried out, for example, at a temperature in the range of about 250° C. to about 600° C., e.g., 310° C. to 500° C., or 350° C. to 480° C., for a variety of contact times, e.g., in the range of 0.1 to 50 seconds, or about 1 to 15 seconds. The molar ratio of oxygen to propylene/isobutylene in the feed can vary, and can be selected by the person of ordinary skill in the art to provide the desired products. In certain embodiments, the acrolein and/or methacrolein can be further reacted (e.g., in a separate process, but without purification) to provide acrylic acid and/or methacrylic acid.

Certain aspects of the disclosure are now explained further via the following non-limiting examples.

EXAMPLES

Comparative Example 1: Conventional Preparation—Cobalt Based Catalyst (Scale 41 g)

A 23.65 mL portion of an aqueous colloidal silica (Nexsil 20NH$_4$) having an SiO$_2$ content of 40 wt % and an average primary silica particle size of 20 nm was mixed with 15.76 mL of an aqueous colloidal silica (Nexsil 85NH$_4$) having an SiO$_2$ content of 40% by weight and an average primary silica particle size of 55 nm. The resultant silica mixture was diluted with 17.10 mL of distilled water and stirred for 5 min to obtain a silica raw material solution (Solution A).

To 45.885 g (33.137 mL) of pre-mixed metal nitrate solution containing Bi(NO$_3$)$_3$ (0.0398M), Ce(NO$_3$)$_3$ (0.1700M), Fe(NO$_3$)$_3$ (0.2851M), Cr(NO$_3$)$_3$ (0.0426M), Mg(NO$_3$)$_2$ (0.3304M), Co(NO$_3$)$_2$ (1.5460M), and Mn(NO$_3$)$_2$ (0.1033M) was added 2.533 mL of concentrated HNO$_3$ (70 wt %), 0.408 mL of KNO$_3$ (1.500M) and 0.350 mL of CsNO$_3$ (1.00M). The resultant solution was stirred for 5 min to obtain a final mixed metal nitrate solution (Solution B).

A 16.848 g portion of (NH$_4$)$_6$Mo$_7$O$_{24}$·4H$_2$O was dissolved in 34.0 mL distilled water to obtain an ammonium molybdate solution (Solution C).

The mixed metal nitrates solution (Solution B) was added to the pre-mixed colloidal silica solution (Solution A) under vigorous stirring. After stirring for 1 min, the ammonium molybdate solution (Solution C) was then added into the above mixture under vigorous stirring. The resulting slurry was stirred for 1 h, followed by wet-milling for another 1 h. The milled slurry was aged with stirring for 16 h. The final slurry contained about 25 wt % metal oxides. Of the total metal oxides, 38 wt % were precipitated while 62 wt % remained in solution. It was found that the precipitate contained more than 70% of the total Mo, Bi, Fe, Cr and Cs that was added. While less than 20 wt % of the total Ce, Mg, Co, Mn, K and Si was present in the precipitate. This experiment was conducted with filtration, calcination and XRF elemental analysis (see Table 2 below). The final slurry was spray dried. The spray dried catalyst precursor was calcined at 250° C. for 45 min, followed by 610° C. for another 45 min. The resulting catalyst composition was Mo$_{12}$Bi$_{0.166}$Ce$_{0.730}$Fe$_{1.185}$Cr$_{0.173}$Mg$_{1.370}$Co$_{6.515}$Mn$_{0.426}$K$_{0.077}$Cs$_{0.044}$O$_x$/50 wt % SiO$_2$.

The pore size distribution of the catalyst was measured by Hg porosimmetry. The total pore volume of pores below 5000 Å was 0.239 mL/g and the fraction of pores having a pore diameter between 1000 Å and 5000 Å was 24.4%. The BET surface area was 31.6 m$^2$/g measured with nitrogen. The packing density of the calcined catalyst was 1.08 g/ml measured using a smaller cylinder. The catalyst attrition was 0.2 measured using a jet cup attrition test (see Table 3 below). By X-ray powder diffraction (XRD), four crystalline phases were observed in the calcined catalyst: α, ß-CoMoO$_4$, Ce$_2$(MoO$_4$)$_3$ and Fe$_2$(MoO$_4$)$_3$ (FIG. 1, and Table 1 below). The ammoxidation of propylene was conducted in a fluid bed reactor using 30 g of catalyst. The propylene conversion was 96.5%, and the acrylonitrile yield was 82.1% at 420° C. and wwh=0.125 h$^{-1}$ (see Table 4 below).

Comparative Example 2: Conventional Preparation—Nickel Based Catalyst (Scale 40 g)

A 22.99 ml portion of an aqueous colloidal silica (Nexsil 20NH$_4$) having a SiO$_2$ content of 40 wt % and an average primary silica particle size of 20 nm was mixed with 15.33 mL of an aqueous colloidal silica (Nexsil 85NH$_4$) having an SiO$_2$ content of 40 wt % and an average primary silica particle size of 55 nm. The resultant silica solution was diluted with 16.6 mL of distilled water and stirred for 5 min to obtain a silica raw material solution (Solution A).

To 3.368 mL of concentrated HNO$_3$ solution (70 wt %) was added 1.360 mL of solution Bi(NO$_3$)$_3$ (1.000M, 2M HNO$_3$), 0.799 mL of Ce(NO$_3$)$_3$ (2.000M), 4.469 mL of Fe(NO$_3$)$_3$ (2.500M), 6.919 mL of Mg(NO$_3$)$_2$ (3.000M), 12.543 mL of Ni(NO$_3$)$_2$ (3.9462M), 0.799 mL of Mn(NO$_3$)$_2$ (2.000M, 0.1M HNO$_3$), 0.371 mL of KNO$_B$ (1.500M) and 0.318 mL of CsNO$_3$ (1.000M). The resulting solution was stirred for 5 min to obtain a final mixed metal nitrate solution (Solution B).

A 16.848 g portion of (NH$_4$)$_6$Mo$_7$O$_{24}$·4H$_2$O was dissolved in 34.0 ml of distilled water to obtain an ammonium molybdate solution (Solution C).

The mixed metal nitrate solution (Solution B) was added to the pre-mixed colloidal silica solution (Solution A) under vigorous stirring. After stirring for 1 min, the ammonium molybdate solution (Solution C) was then added into above the mixture under vigorous stirring. The resulting slurry was stirred for 1 h, followed by wet-milling for another 1 h. The milled slurry was aged with stirring for 16 h. The final slurry contained about 25 wt % metal oxides. Of the total metal oxides, 40 wt % were precipitated while 60 wt % remained in solution. It was found that the precipitate contained more than 80% of the total Mo, Bi, Fe, and Cs that was added. While less than 20 wt % of the total Ce, Mg, Ni, Mn, K and Si was present in the precipitate. This experiment was conducted with filtration, calcination and XRF elemental analysis (Table 2). The final slurry was spray dried. The spray dried catalyst precursor was calcined at 250° C. for 45 min, followed by 630° C. for another 45 min. The resulting catalyst composition was Mo$_{12}$Bi$_{0.171}$Ce$_{0.201}$Fe$_{1.405}$Mg$_{2.610}$Ni$_{6.224}$Mn$_{0.201}$K$_{0.070}$Cs$_{0.040}$O$_x$/50 wt % SiO$_2$.

The pore size distribution of the catalyst was measured by Hg porosimmetry. The total pore volume of pores below 5000 Å was 0.263 mL/g and the fraction of pores having a pore diameter between 1000 Å and 5000 Å was 24.9%. The BET surface area was 31.5 m$^2$/g measured with nitrogen. The packing density of the calcined catalyst was 1.04 g/mL measured using a smaller cylinder. The catalyst attrition was 0.2 measured using a jet cup attrition test (Table 3). By XRD, four crystalline phases, α, ß-NiMoO$_4$, Ce$_2$(MoO$_4$)$_3$ and Fe$_2$(MoO$_4$)$_3$ were observed in the calcined catalyst (FIG. 1). The ammoxidation of propylene was conducted in a fluid bed reactor using 30 g of catalyst. The propylene conversion was 99.5%, and the acrylonitrile yield was 83.2% at 420° C. and wwh=0.140 h$^{-1}$ (Table 4).

Example 3: Nickel-Based Catalyst Prepared by Spray Drying a Homogeneous Solution (Scale 69 g)

Preparation of mixed silica solution: To 68.84 g of an aqueous colloidal silica (Nexsil 20NH$_4$) having a SiO$_2$ content of 40 wt % and an average primary silica particle size of 20 nm was diluted with 153.6 g of distilled water and stirred for 2 min. Under vigorous stirring, the silica solution was then added to 27.52 g of an amorphous silica having primary particle size of 325 mesh and surface area of 80~100 m$^2$/g. The resulting high viscosity gel-like slurry was stirred for 10 min, followed by wet-milling for 0.5 h to yield a cloudy suspension containing 22.03 wt % of SiO$_2$ (Solution A).

Preparation of mixed metal solution: To 42.184 g of a glycolic acid solution (70 wt %) was added 1.471 g of Bi(NO$_3$)$_3$.5H$_2$O with stirring until it was fully dissolved. 23.834 g of (NH$_4$)$_6$Mo$_7$O$_{24}$.4H$_2$O was gradually added to the above solution with vigorous stirring until all of the ammonium molybdate was completely dissolved. The resulting clear solution was stirred for an additional 20 min before adding the following materials: 1.065 g of Mn(CH$_3$COO)$_2$.4H$_2$O, 3.469 g of Mg(CH$_3$COO)$_2$.4H$_2$O, 16.402 g of Ni(CH$_3$COO)$_2$.4H$_2$O, 1.317 g of Ce(NO$_3$)$_3$.6H$_2$O, 4.901 g of Fe(NO$_3$)$_3$.9H$_2$O, 0.295 mL of solution K(CH$_3$COO) (2.7400M) and 0.505 mL of solution CsNO$_3$ (1.000M). The resulting dark solution was stirred for 2 h until a completely clear solution was obtained (Solution B).

Preparation of spray dried catalyst: Solution A was added (187.91 g) to Solution B with stirring to give Solution C. Solution C was a dark green cloudy solution passed through a filter (Whatman™ Filter Paper, Qualitative, 70 mm Ø×100 Circles). No solid was retained on the filter paper (Table 2). The filtered solution contained about 24.4 wt % of oxides-based solids. The final solution was spray dried. The spray dried catalyst precursor was dried at 120° C. for 16 h, and calcined at 250° C. for 45 min, followed by 640° C. for another 45 min in air. The resulting catalyst composition was Mo$_{13.345}$Bi$_{0.30}$Ce$_{0.30}$Fe$_{1.20}$Mg$_{1.63}$Ni$_{6.52}$Mn$_{0.43}$K$_{0.08}$Cs$_{0.05}$O$_x$/60 wt % SiO$_2$.

Figure 2:
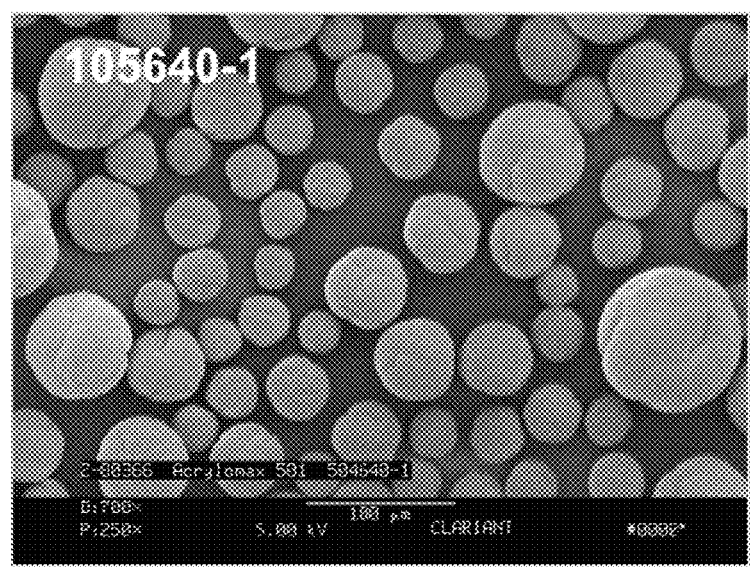
FIG. 2 illustrates scanning electron microscope (SEM) images for the catalysts made by homogeneous spray drying of the metal oxide precursor fluid of Example 3.

The morphology of the solution spray-dried catalyst was basically spherical particles with patched-like surfaces as shown by SEM image analysis (FIG. 2). There was no carbon detected in the final catalyst although some organic materials were used in the synthesis. The pore size distribution of the catalyst was measured by Hg porosimmetry. The total pore volume of pores below 5000 Å was 0.286 mL/g and the fraction of pores having a pore diameter between 1000 Å and 5000 Å was 7.82%. The BET surface area was 41.6 m$^2$/g measured with nitrogen. The packing density of the calcined catalyst was 0.98 g/mL measured using a smaller cylinder. The catalyst attrition was 0 measured using a jet cup attrition test (Table 3). By XRD, three crystalline phases, α- and β-NiMoO$_4$, and Ce$_2$(MoO$_4$)$_3$ were observed in the calcined catalyst (FIG. 1). The ammoxidation of propylene was conducted in a fluid bed reactor using 10 g of the catalyst. The propylene conversion was 98.4%, and the acrylonitrile yield was 85.4% at 420° C. and wwh=0.420 h$^{-1}$ (Table 4).

The results of Examples 1-3 are provided in Tables 1-4 below.

TABLE 1

| | XRD results | | | |
|---|---|---|---|---|
| Catalyst | α-NiMoO$_4$ (%) | β-NiMoO$_4$ (%) | Fe$_2$(MoO$_4$)$_3$ (%) | amorphous (%) |
| Example 1 | 5 | 57 | 38 | 78 |
| Example 2 | 7 | 59 | 33 | 65 |
| Example 3 | 19 | 81 | 0 | 92 |

TABLE 2

Comparison of the ratio of each metal remaining in the precipitate and solution after filtration by use of the heterogeneous and homogeneous methods

| Cat. | method | filtration | Oxides % ratio | Normalized % Ratios of Metals Remaining in the Precipitates and Filtration Solutions | | | | | | | | | | |
| | | | | Mo | Bi | Ce | Fe | Cr | Mg | Co | Ni | Mn | Cs | K | Si |
|---|---|---|---|---|---|---|---|---|---|---|---|---|---|---|---|
| Ex. 1 | heterogeneous | ppt | 37.7 | 86.0 | 100 | 13.7 | 97.9 | 92.0 | 9.8 | 5.3 | | 5..2 | 71.6 | 18.5 | 8.4 |
| | spray-dried | sol. | 62.3 | 14.0 | 0.0 | 86.3 | 2.1 | 8.0 | 90.2 | 94.7 | | 94.8 | 28.4 | 81.5 | 91.6 |
| Ex. 2 | heterogeneous | ppt | 40.2 | 89.3 | 100 | 10.6 | 91.9 | 0 | 9.7 | | 10.3 | 5.9 | 87.6 | 20.1 | 10.0 |
| | spray-dried | sol. | 59.8 | 10.7 | 0.0 | 89.4 | 8.1 | | 90.3 | | 89.7 | 94.1 | 12.4 | 79.9 | 90.0 |
| Ex. 3 | homogeneous | ppt | 0.0 | | | | | | none | | | | | | |
| | spray-dried | sol. | 100 | 100 | 100 | 100 | 100 | | 100 | | 100 | 100 | 100 | 100 | 100 |

TABLE 3

The physical properties measured for the catalysts prepared with heterogeneous spray drying, impregnation and homogeneous spray drying

| Catalyst | Total Pore Vol. range 36 Å < x < 5000 Å (mL/g) | Cumulate Pore Vol. % range 1000 Å < x < 5000 Å (%) | BET (m$^2$/g) | Packing Density (g/mL) | Attrition Test (DI) |
|---|---|---|---|---|---|
| Ex. 1 | 0.239 | 24.4 | 31.6 | 1.08 | 0.2 |
| Ex. 2 | 0.263 | 24.9 | 31.5 | 1.04 | 0.2 |
| Ex. 3 | 0.286 | 7.82 | 41.6 | 0.98 | 0.0 |

TABLE 4

The fluid bed catalytic performances of the catalysts prepared with heterogeneous spray drying, impregnation and homogeneous spray drying

| Catalyst | Support $SiO_2$ (wt %) | WWH | 410° C. | | 420° C. | | 430° C. | |
|---|---|---|---|---|---|---|---|---|
| | | | $C_3H_6$ Conv. (%) | ACN Yield (%) | $C_3H_6$ Conv. (%) | ACN Yield (%) | $C_3H_6$ Conv. (%) | ACN Yield (%) |
| Ex. 1 | 50 | 0.125 | 93.6 | 79.2 | 96.5 | 82.1 | 97.7 | 82.3 |
| Ex. 2 | 50 | 0.140 | 98.6 | 83.2 | 99.5 | 83.2 | 99.8 | 81.1 |
| Ex. 3 | 60 | 0.420 | 97.0 | 85.0 | 98.4 | 85.4 | 99.3 | 83.4 |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A process for producing a catalyst material, the catalyst material comprising
a metal oxide catalyst in an amount in the range of at least about 25 wt %, the metal oxide catalyst having the formula $Mo_xBi_yFe_zA_aB_bC_cD_dO_v$, wherein
x is in the range of 10 to 14;
y is in the range of 0.05 to 5;
z is in the range of 0.2 to 5;
A is at least one element selected from Ni and Co;
a is in the range of 1 to 10;
B is at least one element selected from the lanthanides, Mg, Cr, Mn, Zn and Ca;
b is in the range of 0.01 to 6;
C is at least one element selected from W, Sn, V, Ti, Zr, Ga, Hf, Nb, Ta, In and Al;
c is in the range of 0 to 8;
D is at least one element selected from Li, Na, K, Rb and Cs;
d is in the range of 0.02 to 2; and
v is the number of oxygen atoms required to satisfy the valence requirements of the other component elements Mo, Bi, Fe, A, B, C, and D,
the process comprising:
providing a suspension or slurry of an inert carrier in a metal oxide precursor fluid, the inert carrier having an average particle size less than about 10 microns, the metal oxide precursor fluid comprising a solvent in admixture with a plurality of metal oxide precursors, the plurality of metal oxide precursors comprising at least
a molybdenum oxide precursor,
a bismuth oxide precursor, and
an iron oxide precursor,
wherein less than about 5 wt % of each of the molybdenum oxide precursor, the bismuth oxide precursor, and the iron oxide precursor is not dissolved in the solvent;
spray drying the suspension or slurry of the inert carrier in the metal oxide precursor fluid to obtain a spray-dried precursor material; and
heating the spray-dried precursor material to obtain the catalyst material.

2. The process of claim 1, wherein each of the molybdenum oxide precursor, the bismuth oxide precursor, and the iron oxide precursor are essentially completely dissolved in the solvent.

3. The process of claim 1, wherein the catalyst material further comprises an inert carrier, and wherein the inert carrier is combined with the metal oxide precursor fluid to provide a suspension or slurry of the inert carrier in the metal oxide precursor fluid.

4. The process of claim 1, wherein less than about 1 wt % of each of the molybdenum oxide precursor, the bismuth oxide precursor, and the iron oxide precursor is not dissolved in the solvent.

5. The process of claim 1, wherein the molybdenum oxide precursor is provided as a heptamolybdate.

6. The process of claim 1, wherein the solvent is an aqueous organic acid selected from glycolic acid, acetic acid, lactic acid and mixtures thereof, at a concentration in the range of 45-90 wt %.

7. The process of claim 1, wherein providing a metal oxide precursor fluid comprises:
dissolving a molybdenum oxide precursor and a bismuth oxide precursor in the solvent to obtain a clear solution; and
adding the iron oxide precursor and optionally one or more metal oxide precursors to the clear solution.

8. The process of claim 1, wherein heating includes calcination in the presence of air at a temperature of about 200° C. to about 700° C.

9. The process of claim 1, wherein the inert carrier and the metal oxide catalyst are together present in the catalyst material in an amount of at least about 90 wt %.

10. The process of claim 1, wherein the inert carrier is selected from $SiO_2$, $Al_2O_3$, $ZrO_2$, $Nb_2O_5$, $TiO_2$, $HfO_2$, $Ta_2O_5$, $Sb_2O_5$, and their mixed oxides.

11. The process of claim 1, wherein x is 12.

12. The process of claim 1, wherein
A is Ni, or A is Co, or A is a combination of Ni and Co;
B is at least one element selected from Ce, Mg, Cr, Mn, Zn and Ca;
C is at least one element selected from Sn, V, Ti, Zr, Ga, Hf, Nb, Ta, In and Al; and
D is at least one element selected from Li, K and Cs, and wherein the material does not include W.

13. The process of claim 1, wherein c is substantially zero.

14. The process of claim 1, wherein the metal oxide catalyst has the formula $Mo_xBi_yFe_zNi_aCe_{b1}Mg_{b2}Mn_{b3}K_{d1}Cs_{d2}O_y$, in which x is in the range of 12 to 14, y is in the range of 0.05 to 0.4, z is in the range of 1 to 2.5, a is in the range of 5 to 7, b1 is in the range of 0.2 to 0.6, b2 is in the range of 1 to 3, b3 is in the range of 0.1 to 1.0, d1 is in the range of 0.01 to 0.15, and d2 is in the range of 0.01 to 0.8.

15. The process of claim 1, wherein the catalyst material has an attrition resistance of less than 0.6.

16. The process of claim 1, wherein, of the crystalline content of the catalyst material, no more than 10% is $Fe_2(MoO_4)_3$.

17. A catalyst material prepared by the process according to claim 1.

18. A process for the conversion of propylene, isobutylene, or a mixture thereof to acrylonitrile, methacrylonitrile, or a mixture thereof, the process comprising reacting the propylene, isobutylene, or the mixture thereof with ammonia and oxygen in the vapor phase in contact with a catalyst material according to claim 17.

19. A process for the conversion of propylene, isobutylene, or a mixture thereof to acrolein, methacrolein, or a mixture thereof, the process comprising reacting the propylene, isobutylene, or the mixture thereof with oxygen in the vapor phase in contact with a catalyst material according to claim 17.

20. The process of claim 1, wherein
the solvent is an aqueous organic acid selected from glycolic acid, acetic acid, lactic acid and mixtures thereof, at a concentration in the range of 45-90 wt %; and
less than about 1 wt % of each of the molybdenum oxide precursor, the bismuth oxide precursor, and the iron oxide precursor is not dissolved in the solvent.

21. The process of claim 20, wherein the inert carrier has an average particle size less than about 1 microns.

* * * * *